US012594297B2

(12) United States Patent
Ha

(10) Patent No.: US 12,594,297 B2
(45) Date of Patent: Apr. 7, 2026

(54) COMPOSITION COMPRISING HYALURONIC ACID AND PLURONIC FOR PREVENTING OR TREATING ARTICULAR AND CARTILAGE INJURY

(71) Applicant: Medicrinia, Co., Ltd., Seoul (KR)

(72) Inventor: Yoo Jin Ha, Jeju-si (KR)

(73) Assignee: Medicrinia, Co., Ltd., Seoul (KR)

( * ) Notice: Subject to any disclaimer, the term of this patent is extended or adjusted under 35 U.S.C. 154(b) by 955 days.

(21) Appl. No.: 17/631,680

(22) PCT Filed: Aug. 3, 2020

(86) PCT No.: PCT/KR2020/010215
§ 371 (c)(1),
(2) Date: Jan. 31, 2022

(87) PCT Pub. No.: WO2021/020950
PCT Pub. Date: Feb. 4, 2021

(65) Prior Publication Data
US 2022/0280555 A1      Sep. 8, 2022

(30) Foreign Application Priority Data

Aug. 1, 2019    (KR) ........................ 10-2019-0093748

(51) Int. Cl.
| | |
|---|---|
| A61K 31/728 | (2006.01) |
| A61K 9/06 | (2006.01) |
| A61K 47/36 | (2006.01) |
| A61P 19/02 | (2006.01) |

(52) U.S. Cl.
CPC .............. *A61K 31/728* (2013.01); *A61K 9/06* (2013.01); *A61K 47/36* (2013.01); *A61P 19/02* (2018.01)

(58) Field of Classification Search
CPC ........ A61K 31/728; A61K 9/06; A61K 47/36; A61P 19/02
See application file for complete search history.

(56) References Cited

U.S. PATENT DOCUMENTS

| | | |
|---|---|---|
| 4,716,224 A | 12/1987 | Sakurai et al. |
| 2018/0169298 A1 | 6/2018 | McKinley et al. |

FOREIGN PATENT DOCUMENTS

KR    10-2017-0116811 A    10/2017

OTHER PUBLICATIONS

Jung, Young-seok, et al. "Thermo-sensitive injectable hydrogel based on the physical mixing of hyaluronic acid and Pluronic F-127 for sustained NSAID delivery." Carbohydrate polymers 156 (2017): 403-408. (Year: 2017).*
Lee, Yuhan, et al. "Thermo-sensitive, injectable, and tissue adhesive sol-gel transition hyaluronic acid/pluronic composite hydrogels prepared from bio-inspired catechol-thiol reaction." Soft Matter 6.5 (2010): 977-983. (Year: 2010).*
Venes, Donald. Taber's cyclopedic medical dictionary. FA Davis, 2017, portion of p. 1919. (Year: 2017).*
Entezami, Pouya, et al. "Historical perspective on the etiology of rheumatoid arthritis." Hand clinics 27.1 (2011): 1-10. (Year: 2011).*
Sophia Fox, Alice J., Asheesh Bedi, and Scott A. Rodeo. "The basic science of articular cartilage: structure, composition, and function." Sports health 1.6 (2009): 461-468. (Year: 2009).*
Jung et al., Thermo-sensitive injectable hydrogel based on the physical mixing of hyaluronic acid and Pluronic F-127 for sustained NSAID delivery, Carbohydrate Polymers 156 (2017) 403-408.
Sohn et al., Biomimetic and Photo Crosslinked Hyaluronic Acid/ Pluronic F127 Hydrogels with Enhanced Mechanical and Elastic Properties to be Applied in Tissue Engineering, Macromolecular Research, vol. 24, No. 3, pp. 282-291 (2016).
Nascimento et al., Hyaluronic acid in Pluronic F-127/F-108 hydrogels for postoperative pain in arthroplasties: Influence on physicochemical properties and structural requirements for sustained drug-release, International Journal of Biological Macromolecules 111 (2018) 1245-1254.

* cited by examiner

*Primary Examiner* — Scarlett Y Goon
*Assistant Examiner* — David H Cho
(74) *Attorney, Agent, or Firm* — Kyuoke Lim; Bret E. Field; Bozicevic, Field & Francis LLP

(57)      ABSTRACT

The present invention relates to a hydrogel composition prepared without using a binder. The composition is easy to inject into the human body and has a therapeutic effect on intraarticular lesions and inflammation. The hydrogel of the present invention, which is prepared without a binder, is degraded in an articulation for a long time due to the increased viscoelasticity thereof, thereby enjoying the advantage that the absorption time is prolonged. Therefore, when the hydrogel is used as an injection, its efficacy may be maintained for a long time. Furthermore, the hydrogel has no cytotoxicity, thus showing very high biocompatibility. Particularly when directly injected to an injured site in an articulation, the hydrogel has a therapeutic effect on the intraarticular lesion and inflammation in the corresponding site and thus may be advantageously utilized as a composition for prevention or treatment of an intraarticular lesion and as a viscosity supplement.

9 Claims, 12 Drawing Sheets

HA Only
[Fig. 1A]
Pluronic F-127 Only
[Fig. 1B]
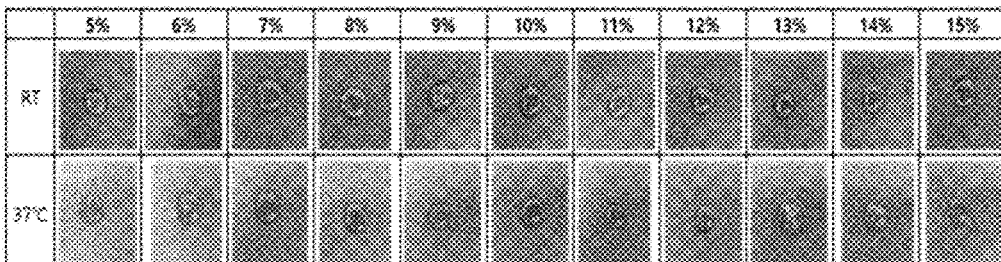

【Fig.2】
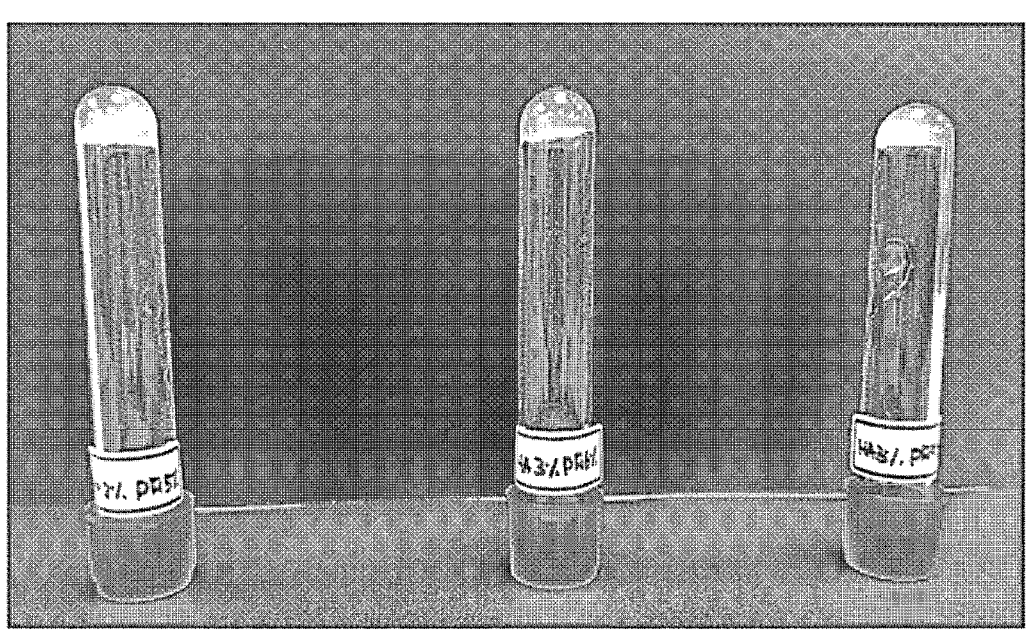

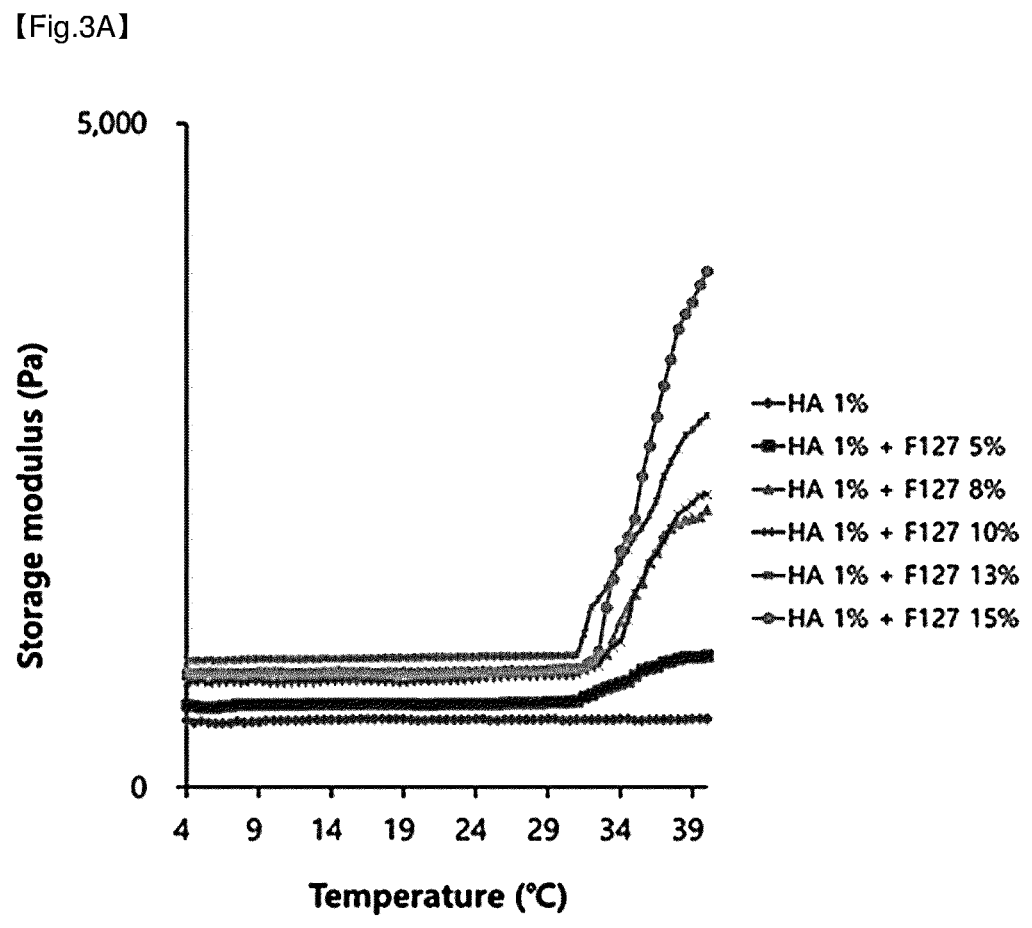

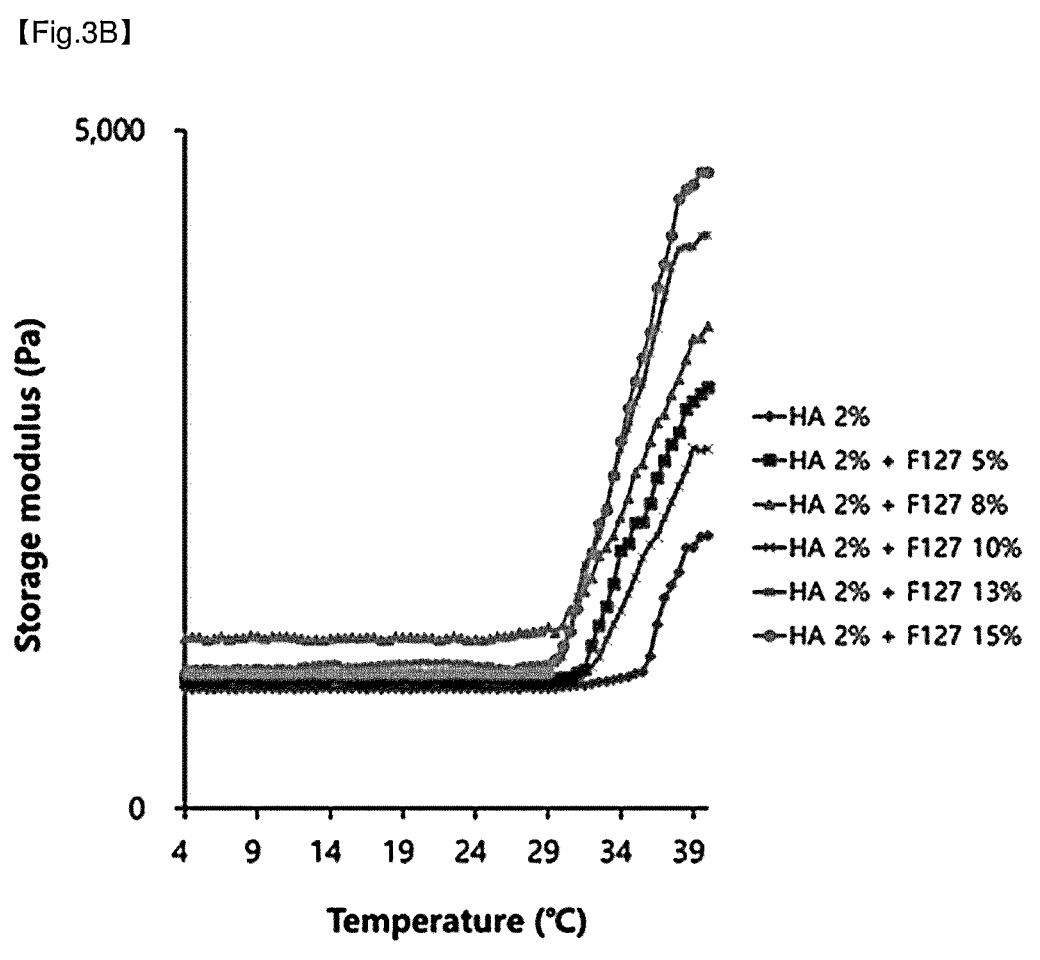

【Fig.3C】
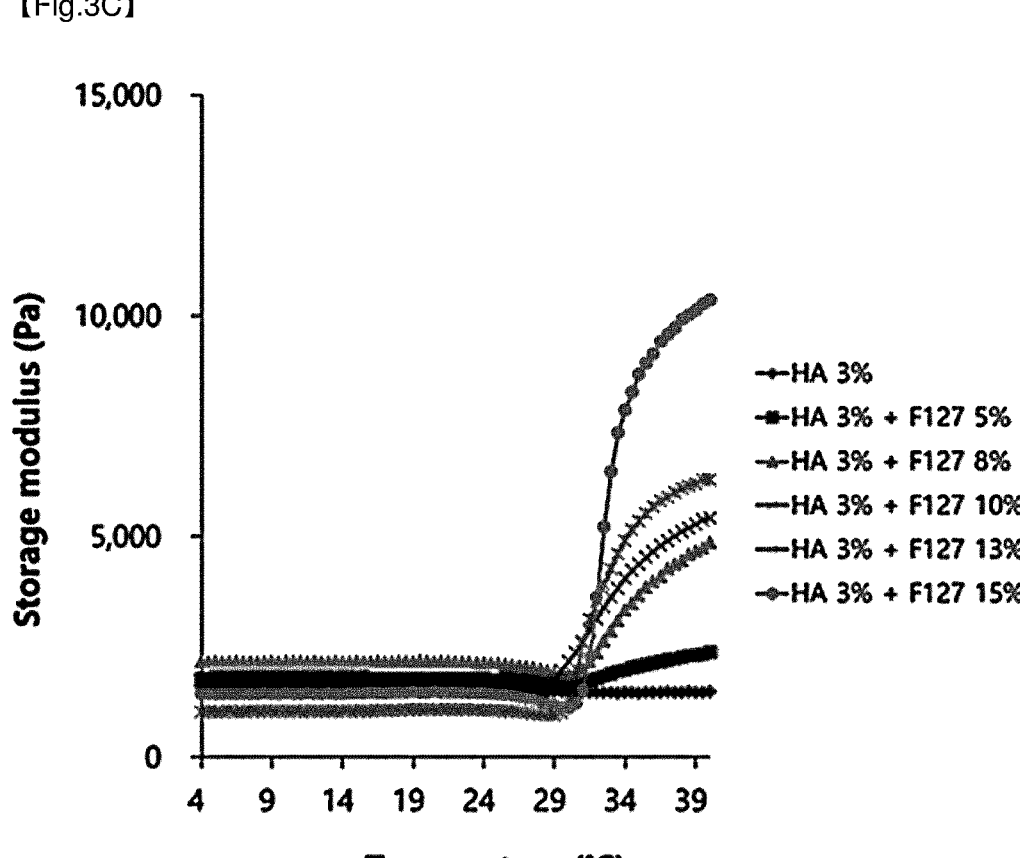

【Fig.3D】
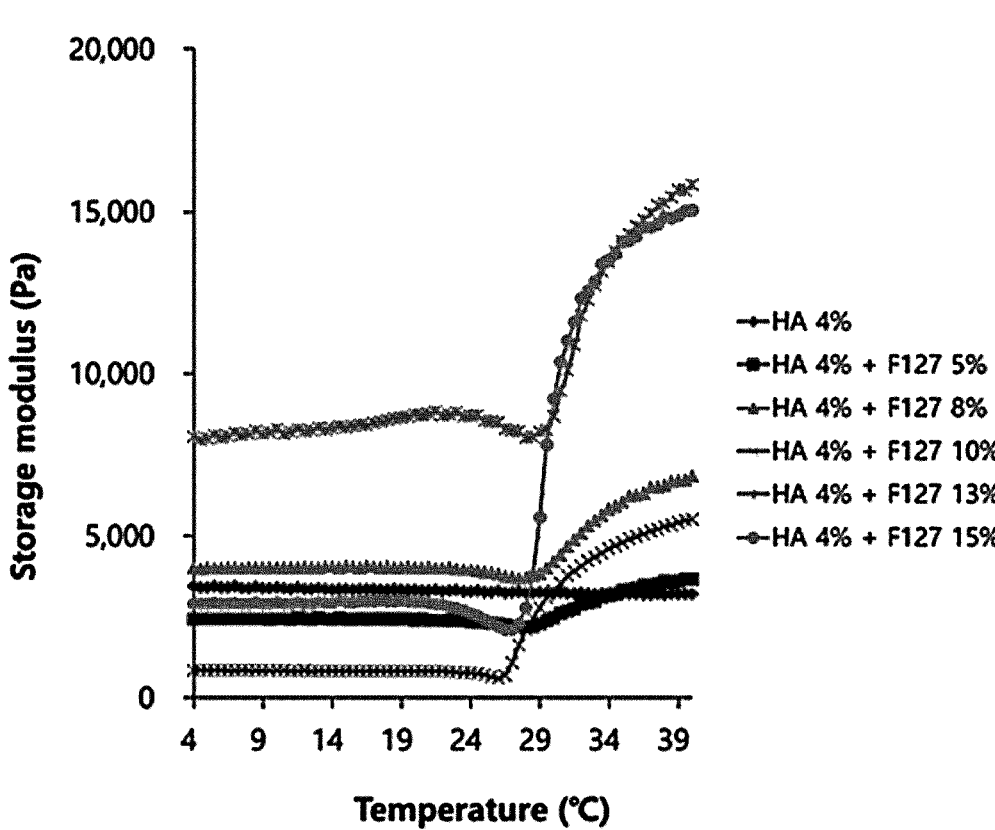

【Fig.3E】
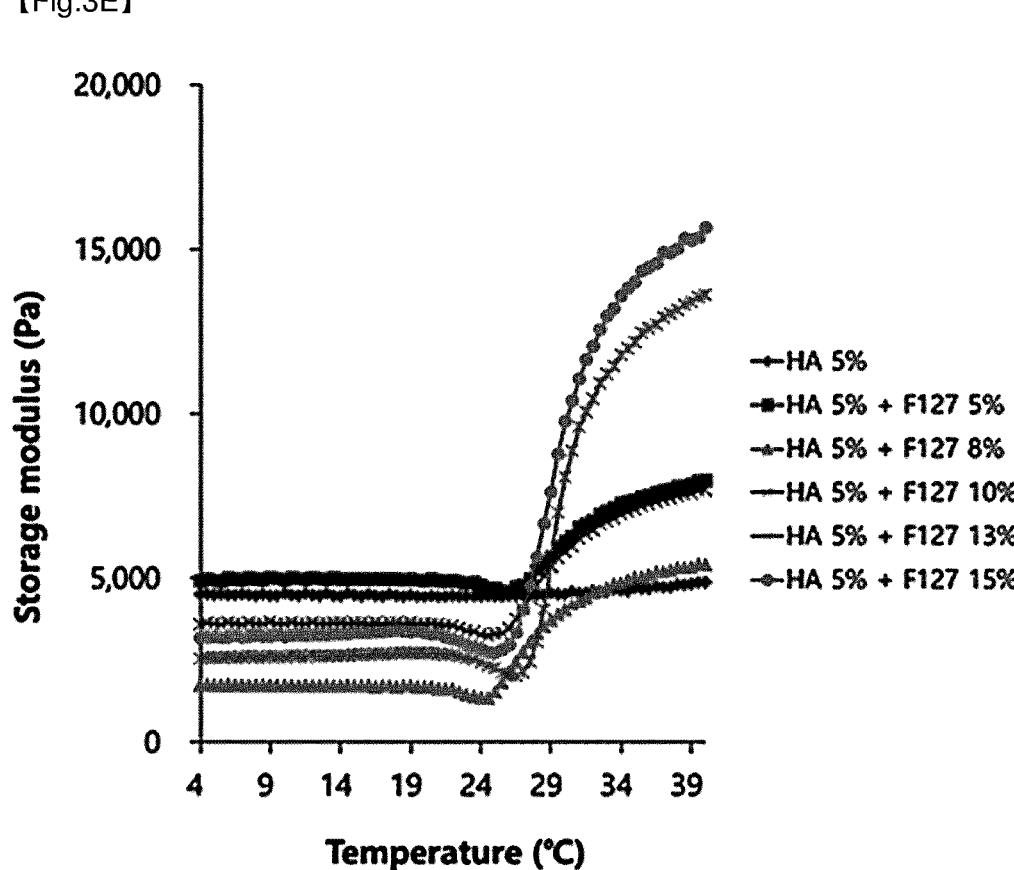

【Fig.3F】
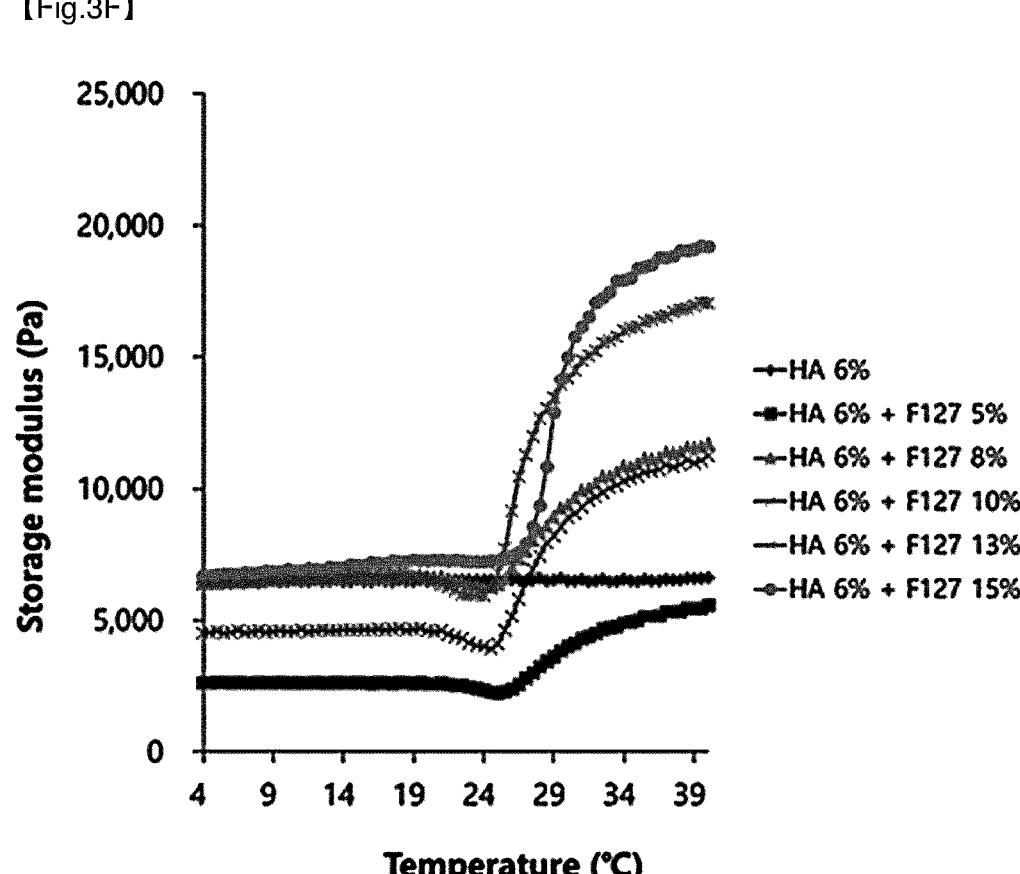

【Fig.4】
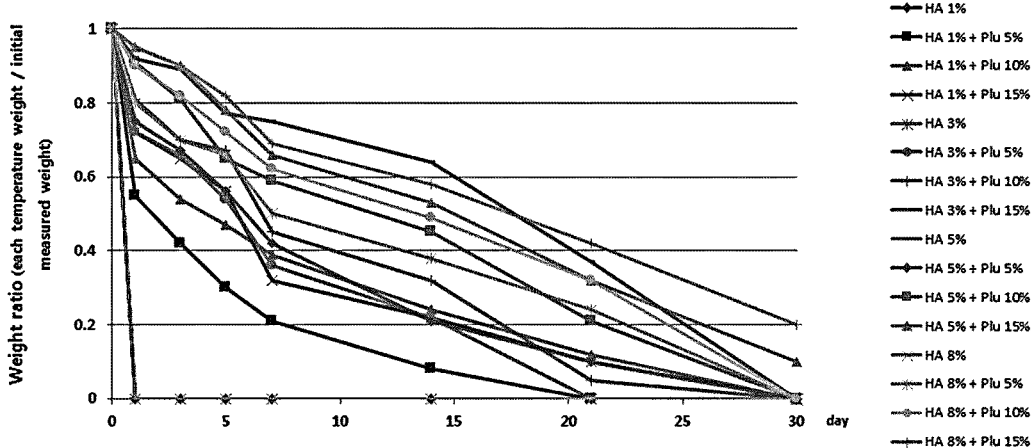

[Fig. 5A]
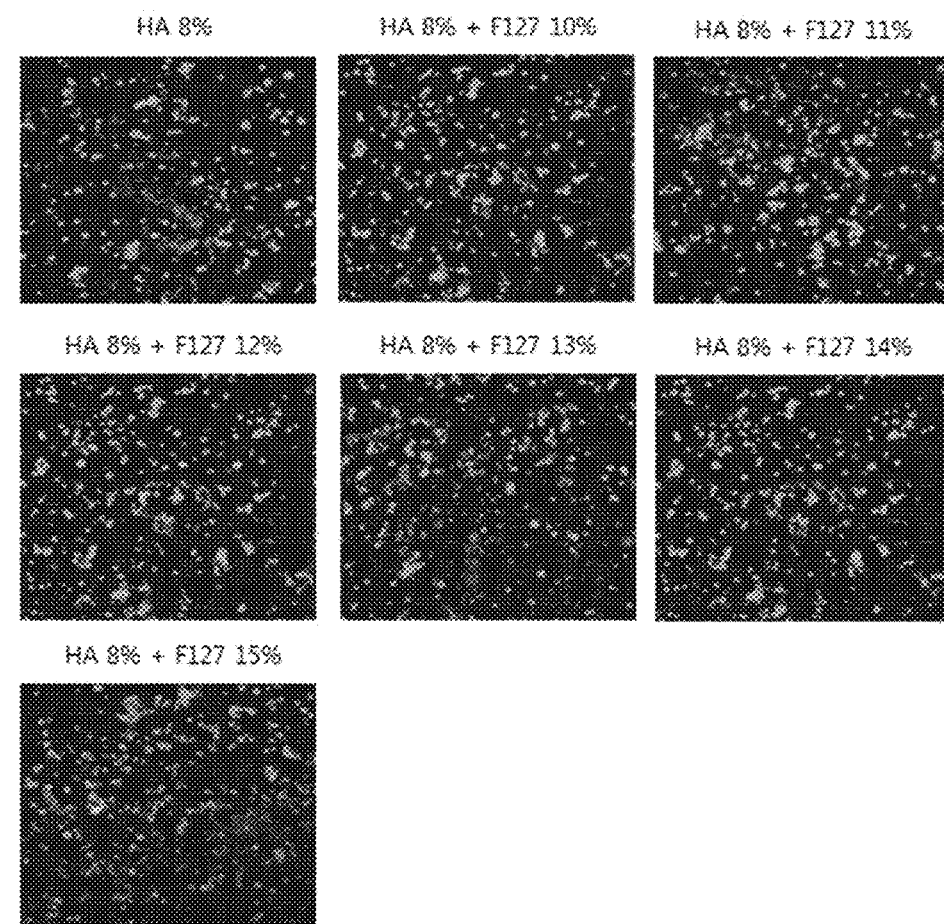
[Fig. 5B]
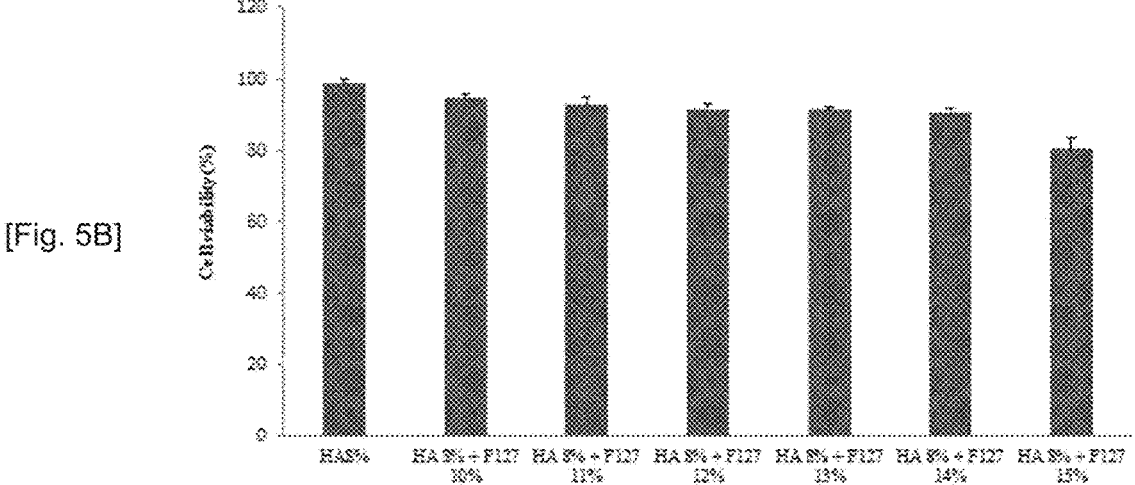

【Fig.6】
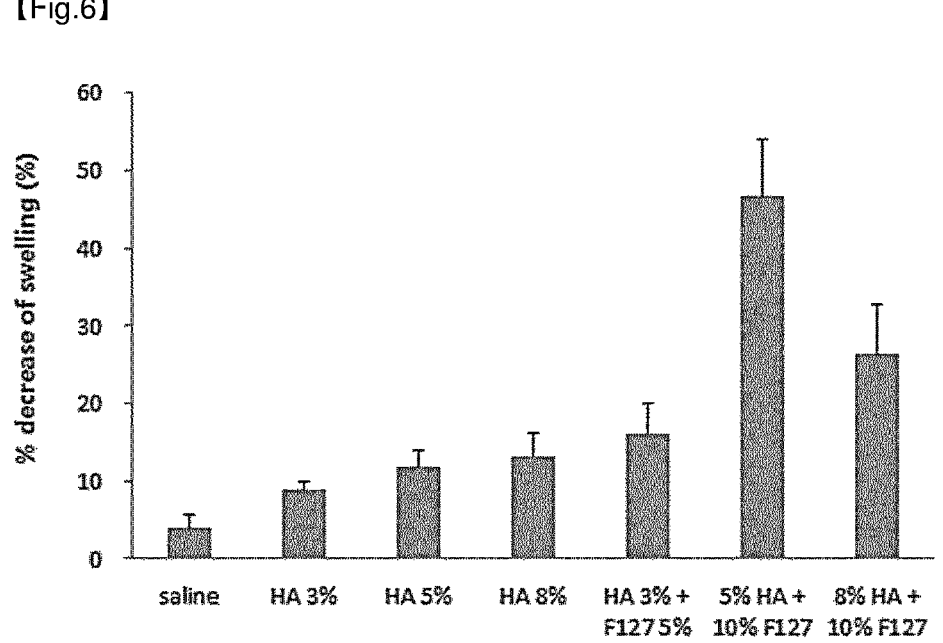

[Fig. 7A]
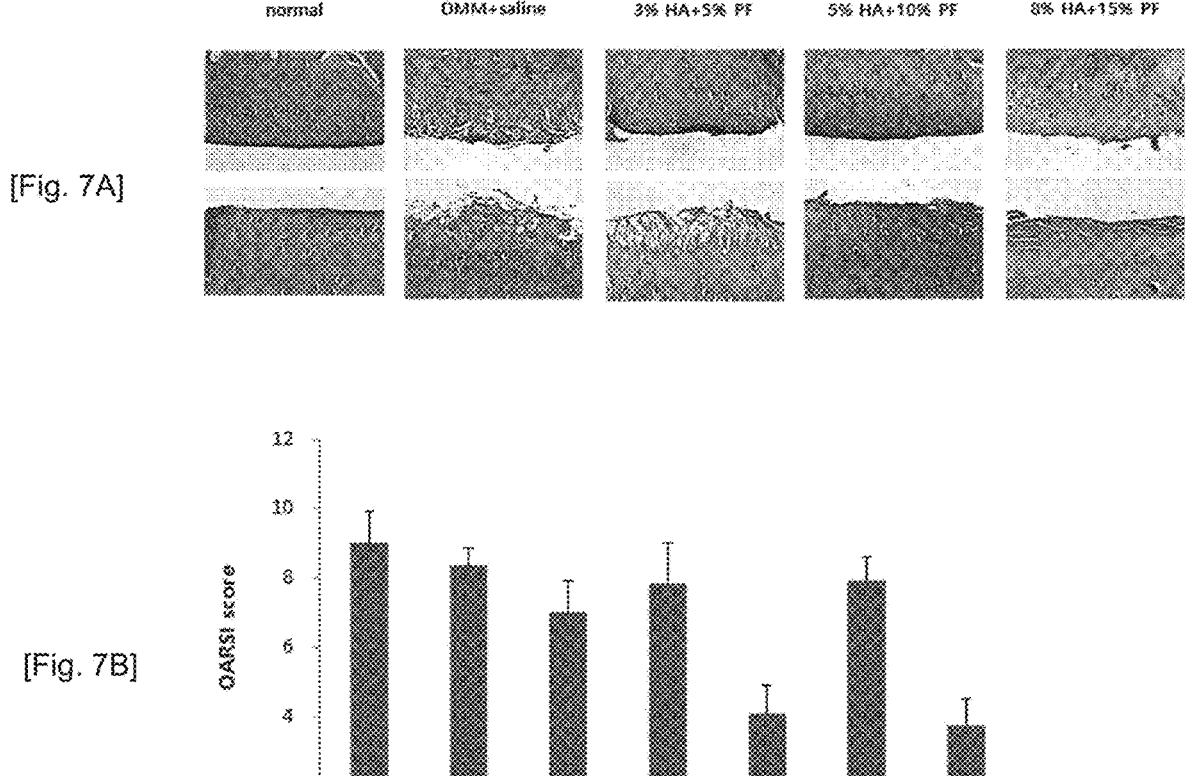
[Fig. 7B]

COMPOSITION COMPRISING HYALURONIC ACID AND PLURONIC FOR PREVENTING OR TREATING ARTICULAR AND CARTILAGE INJURY

TECHNICAL FIELD

The present disclosure relates to a composition for prevention or treatment of intraarticular lesion that is produced without use of a crosslinking agent and is easily injected into a human body, and a production method thereof.

BACKGROUND ART

Osteoarthritis degenerative is a disease in which joint cartilage is worn and degenerative changes occur in a joint. The cause thereof is unknown. It is known that it is deeply related to senescence or excessive weight. For treatment of osteoarthritis, non-pharmacological treatments such as weight loss and exercise therapy may be used along with drug treatment such as non-steroidal anti-inflammatory pain relief drugs. Further, a hyaluronic acid injection which lubricates the joints is recently widely used. As a result, symptom relief and function improvement could be expected.

Low molecular weight HA (Hyruan® Hyaluronan, Artzal® Hylan) applied in clinical practice should be injected 5 times a week, and high molecular weight HA (Hyruan Plus, Aragan Plus, Synvisc®) should be injected 3 times a week. Up to a single dose of XL-HA (Durolane™, Synobian) to slow decomposition as much as possible and maintain its retention in the body has been commercialized.

Hyaluronic acid is a type of mucopolysaccharide involved in producing proteoglycan as a component of a matrix of articular cartilage, and is a glycoprotein complex of N-acetyl-D-glucosamine and D-glucuronic acid linked to each other via a β1-4 glycosidic bond. Hyaluronic acid is a biopolymer material composed of N-acetyl-D-glucosamine and D-glucuronic acid as repeating units linearly connected to each other, and is abundantly present in the vitreous humor of the eye, the synovial fluid of the joints, the cockscombs, and the like. Because of its excellent biocompatibility and viscoelasticity, hyaluronic acid is widely used as medical products and medical instruments such as an ophthalmic surgical adjuvant, drug delivery material, and eye drops, or cosmetics. However, hyaluronic acid itself is easily decomposed in vivo or under conditions such as acid and alkali, and thus its use is limited. Therefore, efforts to develop structurally stable hyaluronic acid derivatives are being widely conducted.

Hyaluronic acid derivatives are being developed for various uses, such as postoperative adhesion prevention agents, wrinkle improving agents, cosmetic aids, drug delivery systems and cell culture scaffolds. In particular, hyaluronic acid derivatives have been actively studied for commercial use such as wrinkle improving agents and cosmetic aids.

As one of the hyaluronic acid derivatives, the cross-linked hyaluronic acid obtained by covalently bonding hyaluronic acids to each other using a cross-linking agent has excellent biocompatibility, physical stability and biodegradability.

However, hyaluronic acid cross-linked products (hyaluronic acid derivatives) produced by conventional methods have relatively low stability against hyaluronic acid degrading enzymes and heat. Further, it is difficult to remove unreacted chemicals for producing the hyaluronic acid cross-linked product. Thus, the hyaluronic acid cross-linked product may not be used as a high-purity biocompatible material. In particular, an example using a polyfunctional epoxide-based crosslinking agent as a crosslinking agent is disclosed in U.S. Pat. No. 4,716,224 in which the cross-linked hyaluronic acid has low physical viscoelasticity and high concentration of the added cross-linking agent, and thus the cross-linking agent may remain in an active state in the product, or a residual amount of unreacted material remaining after the reaction is high, so that the reaction efficiency is low and the purification process is difficult. That is, this method mixes a crosslinking agent and hyaluronic acid with each other in an aqueous alkali solution to induce a crosslinking reaction in a liquid phase. However, in general, the reactivity is very low. Thus, in order to improve the physical properties, it is necessary to increase the reaction concentration or add a larger amount of crosslinking agent. In this case, it is not easy to produce the hyaluronic acid cross-linked product at a high concentration, and there is a problem in that it is difficult to completely remove the crosslinking agent added in a large amount via the purification process.

Therefore, there is a need for a substance that is easily applied to the body and has no toxicity while increasing the stability of hyaluronic acid such that the hyaluronic acid stays in the body for a long time.

DISCLOSURE

Technical Problem

While the present inventors were studying a method to solve the problems of the prior art resulting from the crosslinking agent and to allow the hyaluronic acid to stay in the body for a long time, we identified that mixing of the hyaluronic acid and Pluronic not only allowed the retention time of the hyaluronic acid in the body to be increased, but also allowed the hyaluronic acid to be easily applied as an injection. Furthermore, we identified that a mixture of hyaluronic acid and Pluronic had the therapeutic effects on intraarticular lesions and inflammation. Thus, the present disclosure was completed.

Therefore, a purpose of the present disclosure is to provide a hydrogel composition for the prevention or treatment of intraarticular lesions.

Another purpose of the present disclosure is to provide a method for producing a hydrogel composition for the prevention or treatment of intraarticular lesions.

Another purpose of the present disclosure is to provide a pharmaceutical composition for the prevention or treatment of intraarticular lesions.

Another purpose of the present disclosure is to provide an injectable composition for the treatment of intraarticular lesions.

Another purpose of the present disclosure is to provide a scaffold for the treatment of intraarticular lesions.

Another purpose of the present disclosure is to provide a method for treating injured joints.

Another purpose of the present disclosure is to provide a viscosity supplement composition.

Technical Solution

In order to achieve the above purpose, the present disclosure provides a hydrogel composition for the prevention or treatment of intraarticular lesions, the composition including hyaluronic acid 1 to 10 w/v % and Pluronic 1 to 15 w/v %.

Further, the present disclosure provides a method of producing a hydrogel composition for the prevention or treatment of intraarticular lesions, the method including: 1) preparing a first solution containing 1 to 10 w/v % of hyaluronic acid; 2) preparing a second solution containing 1 to 15 w/v % of Pluronic; and 3) mixing the first solution and the second solution with each other.

Further, the present disclosure provides a pharmaceutical composition for the prevention or treatment of intraarticular lesions, the composition including a hydrogel composition including hyaluronic acid 1 to 10 w/v % and Pluronic 1 to 15 w/v % as an active ingredient.

Further, the present disclosure provides an injection composition for the treatment of intraarticular lesions, the composition including the pharmaceutical composition for the prevention or treatment of intraarticular lesions as an active ingredient.

Further, the present disclosure provides a scaffold for intraarticular lesion treatment including the pharmaceutical composition for the prevention or treatment of the intraarticular lesion as an active ingredient.

Further, the present disclosure provides a method for treating an injured joint, the method including administering to a subject the pharmaceutical composition for the prevention or treatment of the intraarticular lesion.

Further, the present disclosure provides a viscosity supplement composition including a hydrogel composition including 1 to 10 w/v % of hyaluronic acid and 1 to 15 w/v % of Pluronic as an active ingredient.

Advantageous Effects

The hydrogel of the present disclosure has the effect of treating intraarticular lesions and inflammation in the affected area when being directly injected into the injured area of the joint. Thus, the hydrogel of the present disclosure may be usefully used as a composition and viscosity supplement for the prevention or treatment of intraarticular lesions. In particular, the hydrogel of the present disclosure produced without a cross-linking agent has improved biocompatibility, physical properties, and stability against heat and degrading enzymes. Further, it takes a long time to decompose the hydrogel within the joint due to increased viscoelasticity, resulting in a longer absorption time. Therefore, when the hydrogel is used as an injection, the efficacy thereof may be maintained for a long time, and there is no cytotoxicity, and thus the biocompatibility thereof is very good. Therefore, the hydrogel of the present disclosure may be usefully used in various environments in the body, may be easily injected into the body, and may stay in the body for a long time without toxicity.

BRIEF DESCRIPTION OF DRAWINGS

FIGS. 1A-1B are diagrams showing the viscosity according to temperature and concentration of hydrogel composed of sodium hyaluronate alone or Pluronic 127 (F127) alone.

FIG. 2 is a diagram showing the viscosity of hydrogel according to temperature and concentration of sodium hyaluronate and Pluronic 127 (F127) mixture.

FIGS. 3A-3F are diagrams showing the change in viscoelasticity of hydrogel according to concentration and temperature change of sodium hyaluronate alone, sodium hyaluronate and Pluronic 127 (F127) mixture (FIG. 3A is a diagram for sodium hyaluronate 1 w/v %+Pluronic 5, 8, 10, 13 or 15 w/v %, FIG. 3B is sodium hyaluronate 2 w/v %+Pluronic 5, 8, 10, 13 or 15 w/v %, FIG. 3C is a diagram for sodium hyaluronate 3 w/v %+Pluronic 5, 8, 10, 13 or 15 w/v %, FIG. 3D is a diagram for sodium hyaluronate 4 w/v %+Pluronic 5, 8, 10, 13 or 15 w/v %, FIG. 3E is a diagram for sodium hyaluronate 5 w/v %+Pluronic 5, 8, 10, 13 or 15 w/v %, and FIG. 3F is a diagram for sodium hyaluronate 6 w/v %+Pluronic 5, 8, 10, 13 or 15 w/v %.).

FIG. 4 is a diagram identifying the hydrogel decomposition ability by treating a mixture of sodium hyaluronate and Pluronic 127 (F127) with an enzyme.

FIGS. 5A-5B are diagrams identifying the cell survival after 24 hours of the cells mixed with the hydrogel according to the present disclosure.

FIG. 6 is a diagram showing the treatment effect of osteoarthritis inflammation by creating an osteoarthritis MIA (monosodium iodoacetate) model in rats and administering a hydrogel according to the present disclosure thereto.

FIGS. 7A-7B are diagrams showing the degree of osteoarthritis and the treatment results of arthritis by creating an osteoarthritis DMM model in rats and injecting a hydrogel according to the present disclosure thereto after 8 weeks.

MODES OF THE INVENTION

Hereinafter, the present disclosure will be described in detail.

The present disclosure provides a hydrogel composition for the prevention or treatment of intraarticular lesions, the composition including hyaluronic acid and Pluronic.

The hydrogel of the present disclosure may be characterized in that it is produced through mixing of hyaluronic acid and Pluronic, and it is formed without a crosslinking agent. Therefore, hyaluronic acid and Pluronic of the present disclosure may appropriately be mixed with each other within a clinically usable range. Preferably, both may be mixed with each other in an appropriate mixing ratio to increase injection compatibility and increase the retention time in vivo and within a concentration that may obtain a preventive or therapeutic effect on intraarticular lesions.

The present disclosure provides a hydrogel composition for the prevention or treatment of intraarticular lesions, the composition including 1 to 10 w/v % of hyaluronic acid and 1 to 15 w/v % of Pluronic.

Preferably, in the hydrogel of the present disclosure, the hyaluronic acid may be contained in 1 to 9 w/v %, 1 to 8 w/v %, 1 to 7 w/v %, 1 to 6 w/v %, 1 to 5 w/v %, 1 to 4 w/v %, 1 to 3 w/v %, 1 to 2 w/v %, 2 to 10 w/v %, 2 to 9 w/v %, 2 to 8 w/v %, 2 to 7 w/v %, 2 to 6 w/v %, 2 to 5 w/v %, 2 to 4 w/v %, 2 to 3 w/v %, 3 to 10 w/v %, 3 to 9 w/v %, 3 to 8 w/v %, 3 to 7 w/v %, 3 to 6 w/v %, 3 to 5 w/v %, 3 to 4 w/v %, 4 to 10 w/v %, 4 to 9 w/v %, 4 to 8 w/v %, 4 to 7 w/v %, 4 to 6 w/v %, 4 to 5 w/v %, 5 to 10 w/v %, 5 to 9 w/v %, 5 to 8 w/v %, 5 to 7 w/v %, 5 to 6 w/v %, 6 to 10 w/v %, 6 to 9 w/v %, 6 to 8 w/v %, 6 to 7 w/v %, 7 to 10 w/v %, 7 to 9 w/v %, 7 to 8 w/v %, 8 to 10 w/v %, 8 to 9 w/v % or 9 to 10 w/v %. However, the disclosure is not limited thereto.

Further, Pluronic may be contained in 1 to 14 w/v %, 1 to 13 w/v %, 1 to 12 w/v %, 1 to 11 w/v %, 1 to 10 w/v %, 1 to 9 w/v %, 1 to 8 w/v %, 1 to 7 w/v %, 1 to 6 w/v %, 1 to 5 w/v %, 1 to 4 w/v %, 1 to 3 w/v %, 1 to 2 w/v %, 2 to 15 w/v %, 2 to 14 w/v %, 2 to 13 w/v %, 2 to 12 w/v %, 2 to 11 w/v %, 2 to 10 w/v %, 2 to 9 w/v %, 2 to 8 w/v %, 2 to 7 w/v %, 2 to 6 w/v %, 2 to 5 w/v %, 2 to 4 w/v %, 2 to 3 w/v %, 3 to 15 w/v %, 3 to 14 w/v %, 3 to 13 w/v %, 3 to 12 w/v %, 3 to 11 w/v %, 3 to 10 w/v %, 3 to 9 w/v %, 3 to 8 w/v %, 3 to 7 w/v %, 3 to 6 w/v %, 3 to 5 w/v %, 3 to 4 w/v %, 4 to 15 w/v %, 4 to 14 w/v %, 4 to 13 w/v %, 4 to 12 w/v %, 4 to 11 w/v %, 4 to 10 w/v %, 4 to 9 w/v %, 4 to 8 w/v %, 4 to 7 w/v %, 4 to 6 w/v %, 4 to 5 w/v %, 5 to 15 w/v %, 5 to 14 w/v %, 5 to 13 w/v %, 5 to 12 w/v %, 5 to 11 w/v %, 5 to 10 w/v %, 5 to 9 w/v %, 5 to 8 w/v %, 5 to 7 w/v %, 5 to 6 w/v %, 6 to 15 w/v %, 6 to 14 w/v %, 6 to 13 w/v %, 6 to 12 w/v %, 6 to 11 w/v %, 6 to 10 w/v %, 6 to 9 w/v %, 6 to 8 w/v %, 6 to 7 w/v %, 7 to 15 w/v %, 7 to 14 w/v %, 7 to 13 w/v %, 7 to 12 w/v %, 7 to 11 w/v %, 7 to 10 w/v %, 7 to 9 w/v %, 7 to 8 w/v %, 8 to 15 w/v %, 8 to 14 w/v %, 8 to 13 w/v %, 8 to 12 w/v %, 8 to 11 w/v %, 8 to 10 w/v %, 8 to 9 w/v %, 9 to 15 w/v %, 9 to 14 w/v %, 9 to 13 w/v %, 9 to 12 w/v %, 9 to 11 w/v %, 9 to 10 w/v %, 10 to 15 w/v %, 10 to 14 w/v %, 10 to 13 w/v %, 10 to 12 w/v %, 10 to 11 w/v %, 11 to 15 w/v %, 11 to 14 w/v %, 11 to 13 w/v %, 11 to 12 w/v %, 12 to 15 w/v %, 12 to 14 w/v %, 12 to 13 w/v %, 13 to 15 w/v %, 13 to 14 w/v %, or 14 to 15 w/v %. The disclosure is not limited thereto.

According to one embodiment of the present disclosure, the hydrogel according to the present disclosure has excellent intraarticular lesion and inflammation treatment when hyaluronic acid is contained therein at a concentration of about 3 to 8 w/v % and Pluronic is contained therein at a concentration of about 5 to 10 w/v %. In particular, when hyaluronic acid is contained at a concentration of about 4 to 9 w/v % and Pluronic is contained at a concentration of about 10 w/v %, the most excellent osteoarthritis treatment effect is achieved.

Accordingly, the hydrogel composition may contain preferably 1 to 10 w/v %, preferably 4 to 9 w/v % of hyaluronic acid and 1 to 15 w/v %, preferably 9 to 11 w/v % of Pluronic. However, the disclosure is not limited thereto.

According to an embodiment of the present disclosure, when hyaluronic acid is contained at a concentration smaller than the above range, the physical viscoelasticity of the hydrogel may be lowered, such that the intraarticular lesion and inflammation treatment effect of the hydrogel of the present disclosure is lowered. When the hyaluronic acid is contained at a concentration exceeding the above range, the viscoelasticity may be increased, thereby reducing intraarticular injection compatibility and injection efficacy, or continuing discomfort in the joint area after the administration thereof. Further, when Pluronic is contained at a concentration smaller than the above range, physical viscoelasticity may be lowered, thereby reducing injectable compatibility. When the Pluronic is contained in excess of the above range, viscoelasticity may be increased, which may reduce injection compatibility and injection efficacy, and may cause problems in which, after administration, joint discomfort persists or in vivo cytotoxicity is induced.

In fact, when the hyaluronic acid was contained at a concentration of 1% or 2% in the hydrogel of the present disclosure, the hydrogel exhibited a significantly dilute concentration compared to the hydrogel in which the hyaluronic acid was contained at a concentration of 3% or more.

The hyaluronic acid in accordance with the present disclosure may be hyaluronic acid itself or hyaluronic acid salt. The hyaluronic acid salt may be any one or more selected from the group consisting of sodium hyaluronate, potassium hyaluronate, calcium hyaluronate, magnesium hyaluronate, zinc hyaluronate, cobalt hyaluronate, and hyaluronate tetrabutylammonium. The disclosure is not limited thereto.

Further, the term "Pluronic" as used herein refers to the generic class of compounds known as poloxamers and can be used interchangeably with "poloxamer" as a generic name. It is known that the poloxamer is a class of synthetic, nonionic triblock copolymers. It consists of a central hydrophobic block of poly(propylene oxide) (PPO) flanked by two hydrophilic blocks of poly(ethylene oxide) (PEO), arranged in a PEO-PPO-PEO structure. Pluronic in accordance with the present disclosure may include, without limitation, Pluronic known in the art, such as Pluronic F127, Pluronic P123 or Pluronic L44.

In the present disclosure, the intraarticular lesion may be cartilage damage or arthritis.

Cartilage related to lesions and inflammation of the present disclosure refers to hyaline cartilage, fibrocartilage or elastic cartilage. Fibrocartilage is cartilage in which white fibrous tissue and cartilaginous tissue are mixed in various ratios, and although it is strong against pressure, it is well torn and arranged in a dense state. Fibrocartilage exists in connection with hyaline cartilage or connective tissue and functions as a buffer in the area where distortion or compression occurs, enabling limited movement and maintaining elasticity. Hyaline cartilage is mainly composed of type II collagen, and the fibrous component and amorphous material are uniformly observed therein. However, elastic cartilage differs from hyaline cartilage in that it has abundant elastic fibers in the matrix. Therefore, fibrocartilage has a distinct difference from the hyaline cartilage and elastic cartilage in that it has less matrix and more glue fibers and is connected in a regular arrangement. In particular, the collagen of the glue fibers constituting the fibrocartilage is type I collagen. Unlike elastic and hyaline cartilages, the fibrocartilage does not have a distinct perichondrium. It is known that type I glue fiber bundles forming lamellar plates in fibrocartilage are arranged at right angles to neighboring lamellar plates. Unlike other cartilages, due to this characteristic arrangement of fibrocartilage, the fibrocartilage has special elasticity in the discs between the vertebrae, etc. and withstands the pressure generated by weight loads.

In the present disclosure, the cartilage may be hyaline cartilage, various fibrocartilage presents in intervertebral disc or labrum, the joint meniscus, and various elastic cartilage present in the external ear, epiglottis, and some laryngeal cartilage regions. Preferably, the cartilage may be at least one selected from the group consisting of meniscus, articular cartilage, ear cartilage, nasal cartilage, elbow cartilage, knee cartilage, costal cartilage, ankle cartilage, tracheal cartilage, laryngeal cartilage, vertebral cartilage, intervertebral disc, symphysis pubis cartilage, intraarticular fibrocartilage complex, temporomandibular joint cartilage, sternoclavicular joint disc, acetabular fossa cartilage, external ear and epiglottis.

The meniscus is one of the structures that are located between the articular surfaces of the femur and the tibia and play a very important role in maintaining the function of the knee joint, and plays a very important role in distributing the load and stress of the knee joint, absorbing shock, lubricating the articular cartilage, and protecting the articular cartilage by absorbing external shock. The meniscus is made of meniscus-shaped cartilage located in the middle of the knee joint, and the cartilage plate acts as a buffer between the joints and acts as a shock absorber to prevent the body from the damage of the articular cartilage when standing, walking, or running or when body weight is transferred from top to bottom. Therefore, it is known that the cartilage plate is very important in the prevention of degenerative arthritis.

Further, the intraarticular lesions may be caused by one or more diseases selected from the group consisting of degenerative arthritis, rheumatoid arthritis, meniscus damage, intervertebral disc herniation, interpubic disc damage, temporomandibular joint damage, disc damage of the sternoclavicular joint, triangular fibrocartilage complex rupture of the wrist joint, ulnar impaction syndrome, external ear defect, and epiglottis or laryngeal cartilage defect. The disclosure is not limited thereto.

More specifically, the hydrogel composition for the prevention or treatment of intraarticular lesions of the present disclosure may be administered to any one or more diseases selected from the group consisting of degenerative arthritis, inflammatory arthritis, rheumatoid arthritis, osteochondromatosis, distortion, bursitis, menstruation, disc-shaped meniscal tear, meniscus cyst, collateral ligament rupture, anterior cruciate ligament injury, posterior cruciate ligament injury, intraarticular vitreous, exfoliation osteochondritis, plica syndrome, genu varum, valgus (knock-knee), and snapping knee.

The hydrogel composition according to the present disclosure is characterized in that it is injectable with a syringe. The hydrogel of the present disclosure is produced by mixing hyaluronic acid and Pluronic with each other, and thus elasticity and viscosity thereof are improved based on the temperature, so that the suitability for injection is improved. Therefore, the hydrogel of the present disclosure may be used as an injection-type therapeutic agent without surgical operation through high elasticity and viscosity control. In this way, when being formulated into an injection-type therapeutic agent, filler, or injection, the hydrogel of the present disclosure may be suitably used for the treatment of joints injured by abrasion, rupture, degenerative arthritis, and the like.

The hydrogel composition for the prevention or treatment of intraarticular lesions of the present disclosure includes the steps of 1) preparing a first solution containing 1 to 10 w/v % of hyaluronic acid; 2) preparing a second solution containing 1 to 15 w/v % of Pluronic; and 3) mixing the first solution and the second solution with each other.

Each of the first solution and the second solution may employ any solution without limitation as long as each thereof may be dissolved while being harmless to the human body. Depending on the use, each of the first solution and the second solution may be produced using at least one selected from the group consisting of saline solution, distilled water, buffer solution, cosmetic preservative and pharmaceutical preservative, but is not limited thereto. In addition, the solution may further include a physiologically active substance necessary for the treatment of intraarticular lesion and inflammation, and the physiologically active substance may be a growth factor.

Further, the present disclosure provides a pharmaceutical composition for the prevention or treatment of intraarticular lesions, characterized in that the composition contains hyaluronic acid 1 to 10 w/v % and Pluronic 1 to 15 w/v %.

The intraarticular lesion may be a fibrocartilage or elastic cartilage defect. This may refer to a fibrocartilage injury or damage in which fibrocartilage, fibrocartilage tissue and/or joint tissue (synovial membrane, articular membrane, subchondral bone, etc.) is damaged by mechanical stimulation or inflammatory response, or to an elastic cartilage damage or defect due to congenital or acquired factors. The intraarticular lesions may be caused by one or more diseases selected from the group consisting of degenerative arthritis, rheumatoid arthritis, cartilage damage, meniscus damage, intervertebral disc herniation, interpubic disc damage, temporomandibular joint damage, disc damage of the sternoclavicular joint, triangular fibrocartilage complex rupture of the wrist joint, ulnar impaction syndrome, external ear defect, and epiglottis or laryngeal cartilage defect. The intervertebral disc herniation is called a disc, and may occur between the vertebral trunk or between the pubis. The degenerative arthritis and rheumatoid arthritis are diseases that may be caused or aggravated by damage to fibrocartilage or elastic cartilage, and may be treated or improved through damage recovery and regeneration of fibrocartilage or elastic cartilage. In this regard, in the art, for the treatment of early degenerative osteoarthritis of the knee joint, minimal resection is performed during cartilage plate resection. When the cartilage plate defect is severe, surgical methods such as cartilage plate grafting are performed. Thus, the occurrence of degenerative osteoarthritis may be reduced by minimizing or replacing the loss of fibrocartilage or elastic cartilage.

Since the hydrogel of the present disclosure is produced by mixing Pluronic and hyaluronic acid with each other, elasticity and viscosity based on the temperature are improved, thus improving injectability. The present disclosure provides an injection composition for the treatment of intraarticular lesions, the composition including the pharmaceutical composition for the prevention or treatment of the intraarticular lesion as an active ingredient.

The composition of the present disclosure is in the form of a hydrogel composition for cartilage regeneration, and may be effectively administered to a site requiring minimally invasive treatment of injured joints using a syringe or the like. In particular, it may be usefully used in various environments in the body, may be easily injected into the body, and may be used as a support for treatment because it may stay in the body for a long time without toxicity.

Therefore, the present disclosure provides a scaffold for intraarticular lesion treatment including the pharmaceutical composition for the prevention or treatment of the intraarticular lesion as an active ingredient.

In addition, the present disclosure provides a method of treating an injured intraarticular lesion, the method including the step of administering a pharmaceutical composition for the prevention or treatment of the intraarticular lesion to a subject.

As used in the present disclosure, the term "subject" refers to a mammal such as a dog, horses, sheep, pigs, goats, including humans who have intraarticular lesions and whose symptoms may be improved by administering the pharmaceutical composition of the present disclosure thereto. The subject may be preferably a human.

The pharmaceutical composition for the prevention or treatment of intraarticular lesions according to the present disclosure may be used via direct injection or transplantation into a target site, for example, a joint.

Administration of the pharmaceutical composition according to the present disclosure may often be performed at a frequency of daily, weekly, several times per week, bimonthly, several times per month, monthly, or as often as necessary to provide relief of symptoms. In the case of intraarticular use, the amount of the composition administered may be adjusted according to the size of the joint and the severity of the condition. The frequency of subsequent administration to the joint will be spaced according to the time of relapse of symptoms in that joint.

The specific dosage level for any particular patient may be appropriately adjusted depending on a variety of factors including the activity of the composition employed, age, weight, general health, sex, diet, time of administration, route of administration, excretion rate, drug combination, and the severity of the particular disease being treated. The pharmaceutical composition may be produced and administered in dosage units. However, in special circumstances, higher or lower dosage units may be appropriate. Administration of the dosage unit may be carried out by both single administration of the composition and further, multiple administration of divided doses at specific intervals, or administration may be carried out in several smaller dosage units.

In one embodiment, the intraarticular lesion is due to a meniscus injury, and the composition is administered to a joint space, for example, a knee.

For example, an individual with a knee meniscus injury may receive 1, 2, or 3 injections of at least about 2, 3, 4, 5, 6, 7, 8, 9, 10 ml per knee. For other joints, the volume as administered may be adjusted based on the size of the joint.

The pharmaceutical composition of the present disclosure may additionally include a pharmaceutically acceptable carrier in addition to the hydrogel composition contained as an active ingredient. Pharmaceutically acceptable carriers contained in the composition of the present disclosure are those commonly used in formulation, and may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate and mineral oil. The disclosure is not limited thereto. The composition of the present disclosure may further include a lubricant, a wetting agent, a sweetening agent, a flavoring agent, an emulsifying agent, a suspending agent, a preservative, etc. in addition to the above ingredients.

The pharmaceutical composition of the present disclosure may be produced in a unit dose form by formulating using a pharmaceutically acceptable carrier and/or excipient, or may be produced in a multi-dose container, according to a method that may be easily performed by a person of ordinary skill in the art to which the invention pertains. In this case, the formulation may be in the form of a solution, suspension or emulsion in oil or aqueous medium, or may be in the form of an extract, powder, granule, tablet or capsule, and may additionally include a dispersant or stabilizer.

In the present disclosure, the term "treatment" means any action that changes beneficially, such as treatment of intraarticular lesion, inflammation, or joint disease, via administration or application of the composition. Those of ordinary skill in the art to which this application belongs will be able to know the exact criteria for diseases for which the composition of the present application is effective, such as cartilage damage or joint diseases, by referring to the data presented by the Korean Medical Association, etc., and determine the degree of alleviation, improvement, and treatment.

In the present disclosure, the term "prevention" means any action that suppresses or delays the onset of a disease for which the composition is effective via administration of the composition according to the present disclosure. It will be apparent to those skilled in the art that the composition of the present disclosure, which has a therapeutic effect on intraarticular lesion or inflammation, may prevent these diseases when taken or administered before the initial symptoms or appearance of related diseases.

Further, the present disclosure provides a viscosity supplement composition including a hydrogel composition including 1 to 10 w/v % of hyaluronic acid and 1 to 15 w/v % of Pluronic as an active ingredient.

The viscosity supplement is currently the only proven treatment for osteoarthritis with early symptoms. The viscosity supplement means a treatment that supplements the decreased level of hyaluronate in the bursa of a patient with arthrosis by administering one or more injections of hyaluronic acid into the patient's joint.

The above-mentioned contents of the present disclosure are applied identically to each other unless they contradict each other, and appropriate modifications thereof by those of ordinary skill in the art may be included in the scope of the present disclosure.

Hereinafter, the present disclosure will be described in detail through experimental examples and the examples, but the scope of the present disclosure is not limited only to the following experimental examples and the examples.

Example 1. Hydrogel Production

A hydrogel composition was produced for the treatment of lesions and inflammation of injured joints.

1.1 Hydrogel Production Using Sodium Hyaluronate and Pluronic F127

In order to produce hydrogel using sodium hyaluronate and Pluronic F127, a first solution and a second solution were produced. When mixing the first solution and the second solution with each other, the first solution was produced by dissolving sodium hyaluronate (3.3 m$^3$/kg) in saline such that a final concentration of the sodium hyaluronate was 1 w/v % to 10 w/v %, and the second solution was produced by adding and dissolving the Pluronic F127 (BASF) powder into saline such that a final concentration of the Pluronic F127 (BASF) powder was 1 w/v % to 15 w/v % at 4° C.

1.2 Gelation Identification

Sodium hyaluronate alone, Pluronic F127 alone, and the first solution of the sodium hyaluronate and the second solution of Pluronic F127 were mixed with each other. Then, gelation thereof was identified at room temperature and 37° C. conditions. In order to directly identify whether or not gelation occurred, a hydrogel was produced by mixing sodium hyaluronate at a low concentration of 3 w/v % and Pluronic with each other. Absence or presence of the gelation is shown in FIG. 2 (left experimental group: sodium hyaluronate 3 w/v % and Pluronic 5 w/v %, middle experimental group: sodium hyaluronate 3 w/v % and Pluronic 6 w/v %, right experimental group: sodium hyaluronate 3 w/v % and Pluronic 7 w/v %).

As a result, as shown in FIGS. 1A-1B and FIG. 2, in the case of sodium hyaluronate alone, a three-dimensional structure hydrogel was formed through gelation at room temperature and 37° C. However, it was identified that Pluronic F127 alone was in a liquid state at room temperature and 37° C. In addition, it was identified that in the composition obtained by mixing the first solution and the second solution with each other, a three-dimensional structure hydrogel was formed through gelation at both room temperature and 37° C. In particular, through FIG. 2, it was identified that the gelation proceeded when sodium hyaluronate was contained at a low concentration of 3 w/v %.

Example 2. Injectability when Adding Pluronic F127

The injectability properties of hydrogels were identified when Pluronic F127 was added to sodium hyaluronate. Sodium hyaluronate was added so that the final concentration thereof was 1 to 10 w/v %, and Pluronic F127 was added so that the final concentration thereof was 0 w/v % to 15 w/v %. Changes in injectability according to each producing example were identified under room temperature conditions, and the results are shown in Table 1.

TABLE 1

| | | HA | | | | | | | | | |
|---|---|---|---|---|---|---|---|---|---|---|---|
| | | 1% | | 2% | | 3% | | 4% | | 5% | |
| | Series | 21G | 18G | 21G | 18G | 21G | 18G | 21G | 18G | 21G | 18G |
| Plu | 0% | ○ | ○ | ○ | ○ | ○ | ○ | ○ | ○ | ○ | ○ |
| | 5% | ○ | ○ | ○ | ○ | ○ | ○ | ○ | ○ | ○ | ○ |
| | 6% | ○ | ○ | ○ | ○ | ○ | ○ | ○ | ○ | ○ | ○ |
| | 7% | ○ | ○ | ○ | ○ | ○ | ○ | ○ | ○ | ○ | ○ |
| | 8% | ○ | ○ | ○ | ○ | ○ | ○ | ○ | ○ | ○ | ○ |
| | 9% | ○ | ○ | ○ | ○ | ○ | ○ | ○ | ○ | ○ | ○ |
| | 10% | ○ | ○ | ○ | ○ | ○ | ○ | ○ | ○ | ○ | ○ |
| | 11% | ○ | ○ | ○ | ○ | ○ | ○ | ○ | ○ | ○ | ○ |
| | 12% | ○ | ○ | ○ | ○ | ○ | ○ | ○ | ○ | ○ | ○ |
| | 13% | ○ | ○ | ○ | ○ | ○ | ○ | ○ | ○ | ○ | ○ |
| | 14% | ○ | ○ | ○ | ○ | ○ | ○ | ○ | ○ | ○ | ○ |
| | 15% | ○ | ○ | ○ | ○ | ○ | ○ | ○ | ○ | ○ | ○ |

| | | HA | | | | | | | | | |
|---|---|---|---|---|---|---|---|---|---|---|---|
| | | 6% | | 7% | | 8% | | 9% | | 10% | |
| | Series | 21G | 18G | 21G | 18G | 21G | 18G | 21G | 18G | 21G | 18G |
| Plu | 0% | ○ | ○ | ○ | ○ | ○ | ○ | ○ | Δ | ○ | Δ |
| | 5% | ○ | ○ | ○ | ○ | ○ | ○ | X | Δ | X | Δ |
| | 6% | ○ | ○ | ○ | ○ | ○ | ○ | X | Δ | X | Δ |
| | 7% | ○ | ○ | ○ | ○ | ○ | ○ | X | Δ | X | Δ |
| | 8% | ○ | ○ | ○ | ○ | ○ | ○ | X | Δ | X | Δ |
| | 9% | ○ | ○ | ○ | ○ | ○ | ○ | X | Δ | X | Δ |
| | 10% | ○ | ○ | ○ | ○ | ○ | ○ | X | Δ | X | Δ |
| | 11% | ○ | ○ | ○ | ○ | Δ | ○ | X | Δ | X | Δ |
| | 12% | ○ | ○ | ○ | ○ | Δ | ○ | X | Δ | X | Δ |
| | 13% | ○ | ○ | ○ | ○ | Δ | ○ | X | Δ | X | Δ |
| | 14% | ○ | ○ | Δ | ○ | Δ | ○ | X | Δ | X | Δ |
| | 15% | ○ | ○ | Δ | ○ | Δ | ○ | X | Δ | X | Δ |

As a result of measuring injectability, as shown in Table 1 above, in the case of 18 G syringe, injectability was identified in all concentrations of sodium hyaluronate concentration 1 w/v % to 10 w/v % and Pluronic F127 concentration 0 w/v % to 15 w/v %, but in the case of 21 G syringe, when the concentration of sodium hyaluronate increased to 9% or more, the injectability was evaluated as a low level. In particular, it was identified that the convenience of injectability was superior at the concentration of sodium hyaluronate 1 w/v % to 6 w/v % and a concentration of Pluronic F127 0 w/v % to 15 w/v %.

Example 3. Identification of Viscoelasticity Based on Temperature According to Addition of Pluronic F127

When Pluronic F127 was added to sodium hyaluronate, the viscosity characteristics based on the temperature of hydrogel were identified. Sodium hyaluronate was added so as to have a concentration of 1 w/v % to 6 w/v % in the final mixed composition, which exhibited the best injectability convenience. Pluronic F127 was added so that the concentration thereof in the final mixed composition was 5, 8, 10, 13 or 15 w/v %. To measure viscoelasticity according to temperature change, the viscoelasticity was measured using a rheometer (MCR 702, Anton Paar Korea) in a vibration mode using a 25 mm diameter plate (Angular Frequency: 10 rad/s, Shear strain: 1%, gap: 1 mm, temperature rise rate: 2° C./min condition).

Based on a result of measuring the viscosity for each temperature, as shown in FIG. 3A to FIG. 3F, there was no change in the viscosity according to temperature in the case of sodium hyaluronate alone. However, it was identified that the viscosity change appeared according to the concentration of the temperature-sensitive Pluronic F127. Thus, it is more convenient to inject the composition under room temperature conditions such that the composition includes a mixed formulation according to the concentration of Pluronic F127 than when sodium hyaluronate alone is injected. When the hydrogel is administered intraarticularly, the viscosity of the hydrogel increases and thus the therapeutic effect may be maintained longer.

Example 4. Identification of Resolution of Hydrogel as Mixture of Sodium Hyaluronate and Pluronic F127

In order to identify the decomposition capacity of the sodium hyaluronate and Pluronic F127-mixed hydrogel of the present disclosure, the decomposition pattern was measured using a trypsin enzyme. Sodium hyaluronate was added so that the final concentration thereof was 1 to 8 w/v %, and Pluronic F127 was added so that the final concentration thereof was 5 w/v % to 15 w/v %. Based on a result of measuring the resolution, as shown in FIG. 4, in the case of sodium hyaluronate alone, there was a temporal difference in an amount of decomposition based on the concentration. In the case of 1% or 3% thereof, it was difficult to distinguish the form thereof after 6 hours, and in the remaining concentrations, it was difficult to distinguish the gel form as it was entirely decomposed over 24 hours. However, it was identified that hydrogel produced by mixing sodium hyaluronate and Pluronic with each other lasted about 30 days. Therefore, when the hydrogel is administered intraarticularly, the hydrogel produced by mixing sodium hyaluronate and Pluronic with each other has an increased viscosity compared to the hydrogel containing only sodium hyaluronate alone. Thus, the rate of decomposition thereof in the joint cavity may be reduced, and thus the therapeutic effect thereof may be maintained longer.

Example 5. Identification of Cell Viability in Hydrogel as Mixture of Sodium Hyaluronate and Pluronic F127

Cell viability of the sodium hyaluronate and Pluronic F127-mixed hydrogel of the present disclosure was identified to identify the cytotoxicity of the sodium hyaluronate and Pluronic F127-mixed hydrogel of the present disclosure. Sodium hyaluronate was added so that the final concentration thereof was 3 to 8 w/v %, and Pluronic F127 was added so that the final concentration thereof was 10 w/v % to 15 w/v %. To identify cell viability, primary chondrocytes were cultured and mixed with the hydrogel. After staining live and dead cells, respectively, using a Live/Dead assay kit (Invitrogen), the cells were observed using a fluorescence microscope (AMF4300, EVOS, Life Technology). As a result, it was identified that cells survived without apoptosis at most of the concentrations. Four images of the hydrogel obtained by mixing the highest concentration of sodium hyaluronate with a final concentration of 8 w/v % with a final concentration of 10 w/v % to 15 w/v % Pluronic F127 were photographed at 10 magnification. Then, cell viability was calculated and compared using a following formula, and the representative results are shown in FIGS. 5A-5B.

Cell viability=number of viable cells/total number of cells×100

As shown in FIGS. 5A-5B, based on a result of comparing the mixture with sodium hyaluronate alone, the hydrogel further including Pluronic F127 also exhibited almost no red-stained dead cells. It could be identified that in the case of hydrogel produced by mixing 8 w/v % sodium hyaluronate and 15 w/v % Pluronic with each other, 20% normal cells were killed. In addition, based on a result of identifying hydrogel cell survival/death fluorescence images over time, it was identified that in the case of the hydrogel produced by mixing sodium hyaluronate and Pluronic F127 at the concentration of the present disclosure, there was clearly no difference in cell survival compared to the sodium hyaluronate alone hydrogel. Therefore, it was identified that the hydrogel according to the present disclosure not only survives for a long time in the living body when administered in vivo, but also has excellent biocompatibility.

Example 6. Evaluation of Anti-Inflammatory Effect in Animal Model of Osteoarthritis To verify whether the sodium hyaluronate and Pluronic F127-mixed hydrogel of the present disclosure exhibits anti-inflammatory effects in an animal model of osteoarthritis, the following experiment was performed. For this purpose, based on the results as identified in the above examples at various concentrations of sodium hyaluronate and Pluronic mixture, the hydrogel was produced by selecting a concentration that exhibited excellent injectability with suitable viscoelasticity and did not cause apoptosis. Therefore, a hydrogel was produced by mixing sodium hyaluronate 3 w/v % and Pluronic 5 w/v %, a hydrogel was produced by mixing sodium hyaluronate 5 w/v % and Pluronic 10 w/v %, and a hydrogel was produced by mixing sodium hyaluronate 8 w/v % and Pluronic 10 w/v %. In this experiment, the produced hydrogels were used.

First, in order to produce an animal model of osteoarthritis in rats, after performing anesthesia of the rat via injecting with appropriate amounts of Ketamine and Rompun according to the body weight, it was identified that the rat was sufficiently under general anesthesia. Then, the knee joint of the right lower leg thereof was shaved. After the shaving, it was fixed with a band-aid while maintaining the posture. Both knee joints were disinfected with povidone and the knee joint position was identified by palpation of the patella. Then, the osteoarthritis inducing substance, that is, monosodium iodoacetate (monosodium iodoacetate (MIA) (Sigma. Chemical Co. Ltd, Cat. No. 12512, USA)) was diluted with 0.9% saline and the diluted substance was administered into the right knee joint by 50 μl (60 mg/ml) using 31 G 1 ml insulin syringe (BD Medical-Diabetes Care, USA). One week after the induction of osteoarthritis, the diameter of the joint was measured and configured to be at the same size for each group, and 20 μl each of sodium hyaluronate alone and a mixture of sodium hyaluronate and Pluronic F127 was administered once into the joint cavity of the animal model. After identifying that the rats woke up from anesthesia, they were allowed to move freely. After one week after the administration, the diameter of the joint in each group was measured and shown in FIG. 6.

To evaluate the degree of inflammation, the joint swelling caused by inflammatory changes in the joint was used as an inflammatory index. We measured the inner and outer diameters using a precision caliper (Digimatic calipers (Mitutoyo, Japan)), and the measurement was converted to Absolute (right joint diameter-left joint diameter).

As a result, as shown in FIG. 6, in the animal model of osteoarthritis, treatment with sodium hyaluronate alone exhibited an anti-inflammatory effect of about 10 to 15%. A better anti-inflammatory effect was identified in the sodium hyaluronate and Pluronic F127 mixture treatment group. It was observed that in the case of administration of a mixture of sodium hyaluronate and Pluronic F127 of the present disclosure, inflammation was significantly reduced, compared to administration of sodium hyaluronate alone. In particular, the anti-inflammatory effect of the hydrogel composition produced by mixing sodium hyaluronate 5 w/v % and Pluronic 10 w/v % with each other was the best.

Therefore, it may be identified that the anti-inflammatory effect of the hydrogel of the present disclosure is increased via the combination of ingredients, compared to the control group. It was identified that the hydrogel of the present disclosure may be very usefully used as a pharmaceutical agent for the treatment of inflammation occurring in injured joints.

Example 7. Verification of Treatment Effect of Intraarticular Lesion in Animal Model of Osteoarthritis In order to verify whether the sodium hyaluronate and Pluronic F127-mixed hydrogel of the present disclosure exhibits therapeutic effects on the intraarticular lesion in an animal model of osteoarthritis, the following experiment was performed.

First, in order to produce an animal model of osteoarthritis in rats, after performing anesthesia of the rat via injecting with appropriate amounts of Ketamine and Rompun according to the body weight, it was identified that the rat was sufficiently under general anesthesia. Then, the knee joint of both lower legs thereof was shaved. After the shaving, it was fixed with a band-aid while maintaining the posture. Both knee joints were disinfected with povidone and the knee joint position was identified by palpation of the patella. Using a paramedian approach along the incision line passing above and below the knee joint and the medial side of the patella, the inside of the knee joint was accessed. The inside of the joint was observed by bending the knee joint while bending the patella outwardly. After identifying that there were no specific pathological findings, a DMM (destabilization of the medial meniscus) model that damages the medial meniscus was created. The injury site was observed 4 and 8 weeks after induction of the injury, and it was identified that osteoarthritis was induced. Then, using a syringe, 20 μl each of sodium hyaluronate alone or a mixture of sodium hyaluronate and Pluronic F127 produced at the same concentration as in Present Example 6 was injected into the joint cavity of the animal model. After identifying that the rats woke up from anesthesia, they were allowed to move freely, and analgesics and antibiotics were administered thereto for 3 days after surgery. After 8 weeks had elapsed after administration, a section of the joint area where damage and treatment were performed was obtained from each rat and was stained with Safranin O. The degree of osteoarthritis damage was analyzed through quantification using the OARSI score.

As a result, as shown in FIGS. 7A-7B, in the group injected with the sodium hyaluronate and Pluronic F127-mixed hydrogel of the present disclosure, articular cartilage lesions were treated or the progression to osteoarthritis was inhibited 8 weeks after administration, compared to the control hydrogel produced by including only sodium hyaluronate alone. In particular, when a hydrogel composition produced by mixing sodium hyaluronate 5 w/v % and Pluronic 10 w/v % with each other or sodium hyaluronate 8 w/v % and Pluronic 10 w/v % with each other was administered, the degree of damage due to osteoarthritis was the lowest level. Based on these results, it was identified that the injection of sodium hyaluronate and Pluronic F127-mixed hydrogel of the present disclosure into a rat osteoarthritis model could cure articular cartilage lesions or inhibit the progression to osteoarthritis.

Comprehensively, the hydrogel composition produced by mixing hyaluronic acid and Pluronic at an optimal concentration according to the present disclosure exhibited improved injectable compatibility due to the improved elasticity and viscosity based on the temperature, even though it was produced without using a crosslinking agent. Further, the hydrogel composition produced by mixing hyaluronic acid and Pluronic at an optimal concentration according to the present disclosure had the longer retention time in the body and thus the hydrogel composition was highly biocompatible. In particular, the hydrogel composition of the present disclosure has the effect of treating joint lesions or inhibiting the progression to osteoarthritis, and thus it may be usefully used as a composition and a viscosity supplement for the prevention or treatment of intraarticular lesions.

The invention claimed is:

1. A method for treatment of an intraarticular lesion, the method comprising administering a hydrogel composition for the prevention or treatment of the intraarticular lesion to a subject, wherein the composition comprises 4 to 9 w/v % of hyaluronic acid and 9 to 11 w/v % of poloxamer.

2. The method for treatment of an intraarticular lesion of claim 1, wherein the hyaluronic acid is hyaluronic acid salt.

3. The method for treatment of an intraarticular lesion of claim 2, wherein the hyaluronic acid salt is at least one selected from a group consisting of sodium hyaluronate, potassium hyaluronate, calcium hyaluronate, magnesium hyaluronate, zinc hyaluronate, cobalt hyaluronate, and hyaluronate tetrabutylammonium.

4. The method for treatment of an intraarticular lesion of claim 1, wherein the intraarticular lesion is cartilage injury or arthritis.

5. The method for treatment of an intraarticular lesion of claim 4, wherein the cartilage is hyaline cartilage, fibrocartilage or elastic cartilage.

6. The method for treatment of an intraarticular lesion of claim 4, wherein the cartilage includes at least one selected from a group consisting of meniscus, articular cartilage, ear cartilage, nasal cartilage, elbow cartilage, knee cartilage, costal cartilage, ankle cartilage, tracheal cartilage, laryngeal cartilage, and vertebral cartilage.

7. The method for treatment of an intraarticular lesion of claim 1, wherein the intraarticular lesion is caused by at least one disease selected from a group consisting of degenerative arthritis, rheumatoid arthritis, meniscus damage, intervertebral disc herniation, interpubic disc damage, temporomandibular joint damage, disc damage of a sternoclavicular joint, rupture of a triangular fibrocartilage complex of a wrist joint, ulnar impaction syndrome, external ear defect and epiglottis or laryngeal cartilage defect.

8. The method for treatment of an intraarticular lesion of claim 1, wherein the hydrogel composition is a viscosity supplement composition.

9. The method for treatment of an intraarticular lesion of claim 1, wherein the hydrogel composition is injectable with a syringe.

* * * * *